United States Patent [19]

Ueno et al.

[11] Patent Number: 5,285,223
[45] Date of Patent: Feb. 8, 1994

[54] OPHTHALMIC OPTICAL APPARATUS HAVING AN ALIGNMENT OPTICAL SYSTEM

[75] Inventors: Yasunori Ueno, Kawasaki; Masanobu Kaneko, Yokohama, both of Japan

[73] Assignee: Nikon Corporation, Tokyo, Japan

[21] Appl. No.: 933,096

[22] Filed: Aug. 21, 1992

[30] Foreign Application Priority Data

Aug. 30, 1991 [JP] Japan .................................. 3-244233

[51] Int. Cl.⁵ ................................................ A61B 3/14
[52] U.S. Cl. ...................................... 351/208; 351/211
[58] Field of Search ................ 351/208, 211, 212, 221

[56] References Cited

U.S. PATENT DOCUMENTS

| | | | |
|---|---|---|---|
| 3,842,254 | 8/1973 | Dianetti | 351/212 |
| 4,264,153 | 4/1981 | Ito | 351/208 |
| 4,499,897 | 2/1985 | Roussel | 128/303.1 |
| 4,564,273 | 1/1986 | Iba et al. | 351/208 |
| 4,673,264 | 6/1987 | Takahashi | 351/208 |
| 4,848,896 | 7/1989 | Matsumoto | 351/211 |
| 4,917,486 | 11/1990 | Rinklake et al. | 408/180 |
| 5,101,826 | 4/1990 | Katsuragi | 351/208 |

Primary Examiner—Richard A. Bertsch
Assistant Examiner—Richard A. Basichas
Attorney, Agent, or Firm—Shapiro and Shapiro

[57] ABSTRACT

An ophthalmic optical apparatus having an alignment optical system comprises two conical optical elements for forming an alignment light beam into a ring-shaped collimated light beam centered on an optical axis and directing it to a focusing optical system, an in-focus state is determined based on a light pattern formed by the focusing optical system from the ring-shaped collimated light beam on an object plane.

11 Claims, 5 Drawing Sheets

OPHTHALMIC OPTICAL APPARATUS HAVING AN ALIGNMENT OPTICAL SYSTEM

BACKGROUND OF THE INVENTION

1. Field of the Invention

The present invention relates to an ophthalmic optical apparatus for observing and treating an eye, and more particularly to an ophthalmic optical apparatus having an alignment optical system for treating the eye.

2. Related Background Art

For a series of ophthalmic diseases including, inter alia, retina disease, a high density laser radiation or a so-called photo-coagulation laser is used to treat a diseased part and it is irradiated to the diseased part as a light spot. An irradiation output, an irradiation time and a spot size of the photo-coagulation laser are varied depending on a photo-coagulation operation to a particular diseased part. It is very important to focus the photo-coagulation laser to the diseased part, and to this end a proper alignment system is required. In a prior art alignment system, an alignment beam to be used for the alignment is split into two or more light beams which are collected and combined to attain exact focusing.

For example, in an ophthalmic optical apparatus (laser photo-coagulation apparatus) for observation and treatment which uses a laser, disclosed in U.S. Pat. No. 4,499,897, particularly in FIG. 5 thereof, an alignment laser beam 22 which is a visible ray generated by a laser oscillator 21 in the laser photo-coagulation apparatus 20 is split into two parallel light beams 22a and 22b by a pair of semi-transmissive prisms (beam splitter) 23, and those light beams pass through a first beam splitter (dichroic mirror) 24, are reflected by a ring-shaped outer periphery of a second beam splitter (dichroic mirror) 25 and directed to an object (an eye of a patient), not shown, through a focusing lens 26 so that they are focused on the object plane.

In this case, an in-focus state is attained at a point where the two light beams 22a and 22b coincide. When they are focused on the object plane, one spot pattern h is formed, and when they are not focused, two spot patterns g and i are formed.

On the other hand, a photo-coagulation light 29 for treatment which is generated by another laser oscillator 28 passes through a beam expander 30 so that it is expanded to a light beam having a diameter which is slightly smaller than a gap between the two alignment light beams 22a and 22b. The expanded photo-coagulation light is reflected by the first beam splitter (dichroic mirror) 24, follows the same light path as that of the alignment laser beam 22, is further reflected by the second beam splitter 25 and is directed to the object through the focusing lens 26 so that it is focused at the coincident point of the two beams 22a and 22b of the alignment laser beams 22, that is, at the same point as the point on the object plane at which the spot pattern h is formed.

In the laser photo-coagulation apparatus 20, the prism 23 is rotated so that the two light beams 22a and 22b are rotated around an optical axis of the photo-coagulation light 29. When the photo-coagulation light 29 is generated by the laser oscillator 28 after the in-focus state has been confirmed, the photo-coagulation light 29 follows the same light path as that of the alignment laser beam 22 and it is focused at the same point as the point on the object plane at which the spot pattern h of the alignment laser beam 22 is formed in the in-focus state so that the diseased part is treated.

In the prior art ophthalmic optical apparatus (laser photo-coagulation apparatus) for observation and treatment, since the two alignment light beams 22a and 22b which go along the outer periphery of the photo-coagulation light 29 are rotated around the optical axis of the photo-coagulation light 29, the construction is complex, a relatively long time is required for the alignment, the process to generate the photo-coagulation light 29 is complex and a long time is required for the treatment.

U.S. Pat. No. 4,917,486 discloses a laser photo-coagulation apparatus in which, instead of rotating the two alignment light beams, a mask having four apertures centered at an optical axis and arranged at an angular pitch of 90° is provided on an alignment light path of a collimated light beam, the four collimated light beams transmitted through the apertures of the mask are used as the alignment light beams which go along the outer periphery of the treatment light beam, and the in-focus state on the object plane is determined by the coincidence state of the four spot patterns formed by the four light beams.

However, in the laser photo-coagulation apparatus disclosed in U.S. Pat. No. 4,917,486, only those portions of the light generated by the alignment light source which are transmitted through the four apertures formed in the mask can be used as the alignment light beams and hence energy is wasted.

In the alignment system of the prior art laser photo-coagulation apparatus, the light beam is split into two or four parallel alignment light beams by the prism and they form the predetermined spot pattern at the in-focus state to permit the detection of the in-focus state. However, the position precision of the prism is hard to attain. Further, the entire construction of the optical system is complex and the prism cost is expensive.

SUMMARY OF THE INVENTION

It is an object of the present invention to provide an ophthalmic optical apparatus which solves the above problems, attains exact focusing with a very simple alignment optical system, can confirm status of a light path through which a treatment light beam passes and attains the alignment rapidly and easily.

In order to achieve the above object, the ophthalmic optical apparatus having the alignment optical system in accordance with the present invention comprises means for generating a treatment laser light beam; means for generating an alignment light beam having a different wavelength than that of the treatment light beam; a focusing optical system for focusing the treatment light beam and the alignment light beam onto an object plane of an eye to be treated; and cone lens means having two conical planes for expanding the alignment light beam to a collimated light beam having a ring-shaped cross section along a periphery of the treatment light beam. The cone lens means includes a first conical plane arranged on the alignment optical axis for refracting the alignment light beam and expanding the same to a conical light beam centered on the optical axis, and a second conical plane for refracting the conical light beam, forming the same into a ring-shaped collimated light beam parallel to the optical axis and directing the same to said focusing optical system. Thus, the alignment light beam is formed into a small light spot pattern in an in-focus state and into a ring-shaped light pattern centered on the optical axis in a defocus state.

It is preferable that the cone lens means can vary a distance between the two conical planes in order to vary a ring diameter of the ring-shaped collimated light beam.

It is further preferable to obliquely arrange a reflection mirror on an alignment optical axis inside the ring-shaped collimated light beam and direct the treatment laser beam to the focusing optical system through the reflection mirror.

In the ophthalmic optical apparatus of the present invention thus constructed, the exact focusing is attained, the status of the light path through which the treatment light beam passes can be confirmed, and the alignment is made rapidly and with ease.

Other objects, features and advantages of the present invention will be apparent from the following detailed description taken in conjunction with the accompanying drawings.

DETAILED DESCRIPTION OF THE PREFERRED EMBODIMENTS

One embodiment of the present invention is now explained in detail with reference to the accompanying drawings.

Figure 1:
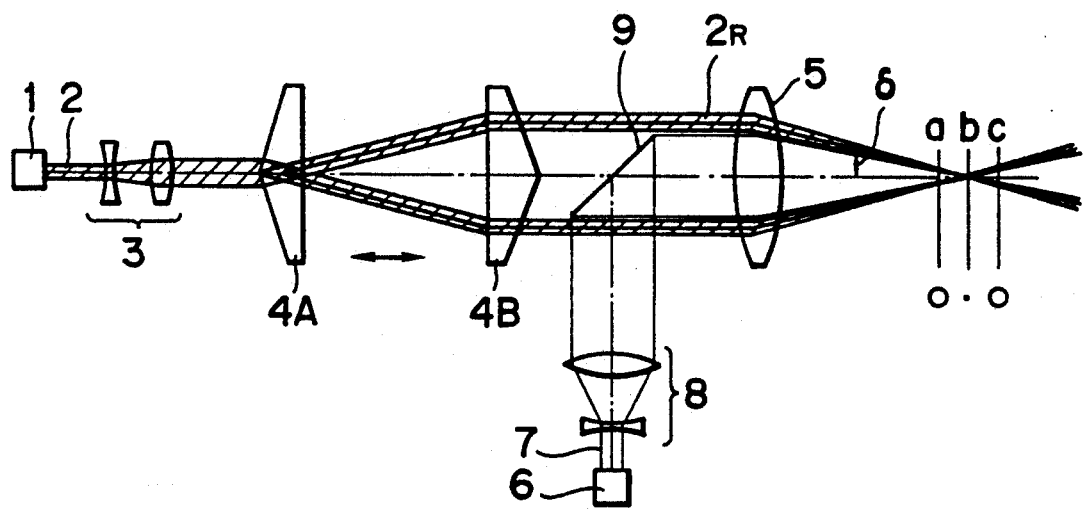
FIG. 1 shows a schematic construction of an optical system and a sectional view of a light path in one embodiment of the present invention.

FIG. 1 shows a schematic construction of an optical system having an alignment optical system with a cone lens in an embodiment of the photo-coagulation apparatus of the present invention. In FIG. 1, an alignment beam 2 emitted from an alignment laser oscillator 1 is expanded by a beam expander 3 to a light beam having a circular cross-section of a predetermined diameter, and it is further expanded to a ring-shaped collimated light beam by a first cone lens 4A and a second cone lens 4B arranged on an optical axis and then it is directed to a focusing lens 5. The first cone lens 4A is a flat-convex cone lens having a conical convex plane faced to the light source. The alignment light beam directed to the first cone lens 4A is refracted by the conical convex plane of the first cone lens 4A and expanded to a conical light beam. The second cone lens 4B is a flat-convex cone lens having a conical convex plane faced to the focusing lens 5. The alignment light beam directed to the second cone lens 4B is refracted by the conical convex plane of the second cone lens 4B and formed into a ring-shaped collimated light beam 2R.

The ring-shaped collimated light beam 2R is focused by the focusing lens 5 to a plane of an object (not shown) which is to be ophthalmically treated. In an in-focus state, it is a point on a focal plane of the focusing lens 5 so that a small and bright light spot pattern b is formed on the object plane. In an out-of-focus state, a ring-shaped light pattern a or c is formed on the object plane and the diameter of the ring varies with the amount of defocusing accordingly, it is a point in the in-focus state and the brightness of the spot abruptly increases. This facilitates the detection of the in-focus state.

On the other hand, a photo-coagulation light 7 for treatment having a different waveform than that of the alignment light 2, which is emitted by a treatment laser oscillator 6 passes through a beam expander 8 and is expanded to a collimated light beam having a predetermined cross-section diameter. It is reflected by a mirror 9 obliquely arranged on an alignment optical axis inside of the alignment ring-shaped collimated light beam 2R, and then it follows the same light path as that of the alignment light beam and is directed to the focusing lens 5. In this case, a main optical axis of the photo-coagulation light coincides with the alignment optical axis which passes through the focusing lens 5. The photo-coagulation light directed to the focusing lens 5 is focused by the focusing lens 5 to the same position on the object plane as that at which the light spot b is formed by the alignment light beam so that the treatment photo-coagulation light spot is formed. Accordingly, in the treatment, the light spot pattern b by the alignment light beam is set at the predetermined position on the plane of object to be ophthalmically treated, and when the in-focus state is detected, the photo-coagulation light 7 is generated by the treatment laser oscilator 6.

The larger an incident angle δ to the object plane of the eye is, the higher is the precision of detection of the in-focus state. Accordingly, the larger the ring diameter of the ring-shaped collimated light beam of the alignment light is, the higher is the precision of the in-focus state detection. In the present embodiment, the two conical planes are formed by the two separate flat-convex cone lenses 4A and 4B and at least one of the cone lenses is movable along the optical axis to allow the adjustment of the distance between the two conical planes. Accordingly, by changing the distance between the cone lenses 4A and 4B, the ring diameter of the ring-shaped colliminated light beam may be increased and the precision of the detection of the in-focus state is enhanced. Since the ring-shaped light pattern abruptly changes the bright light spot, the detection of the in-focus state is facilitated.

In the present embodiment, since the treatment photo-coagulation light and the alignment light are directed to the focusing lens 5 through the common optical axis, if the numerical apertures of the alignment light and the photo-coagulation light are substantially equal, the spot size by the alignment light in the in-focus state and the spot size of the photo-coagulation light are substantially equal. Accordingly, the treatment position on the object plane and the size thereof can be estimated at the time of alignment.

Figure 2:
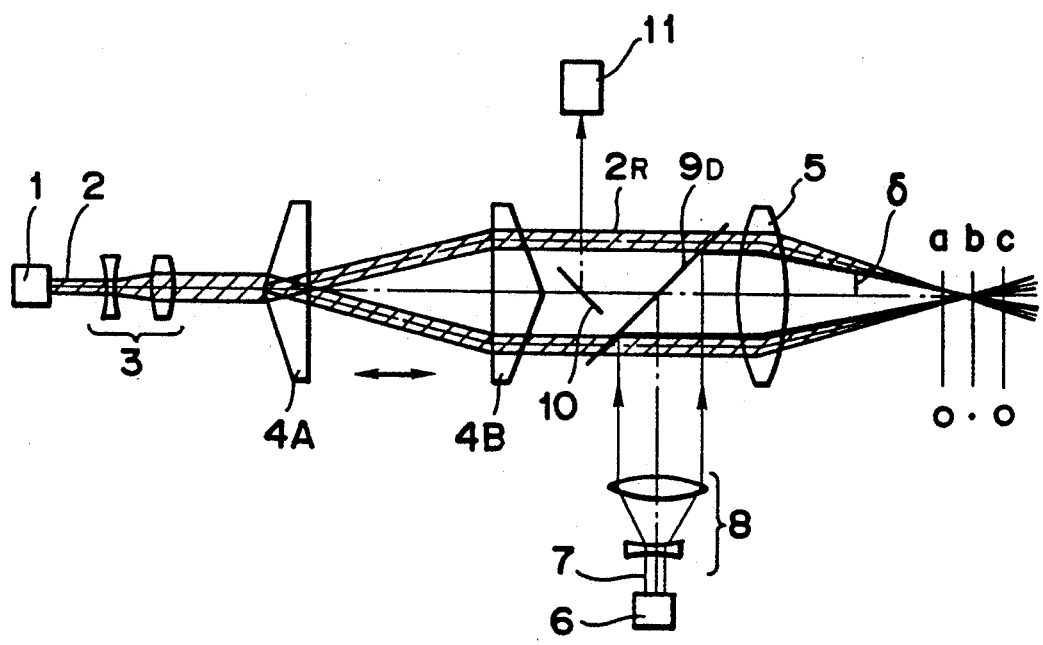
FIG. 2 shows a schematic construction of an optical system and a sectional view of a light path in another embodiment of the present invention.

FIG. 2 shows a schematic structure of an optical system in another embodiment of the present invention which has an alignment optical system including cone lenses. It is basically identical to the embodiment of FIG. 1 except a construction of a mirror which directs the photo-coagulation light to the focusing lens and the addition of an observation optical system, and the like elements are designated by the like numerals and the detailed explanation thereof is omitted.

In FIG. 2, the treatment photo-coagulation light 7 emitted by the treatment laser oscillator 6 is expanded by the beam expander 8 to a light beam having a predetermined cross-section diameter. The expanded photo-coagulation light is reflected by a dichroic mirror 9D obliquely arranged on the alignment optical axis so that it crosses an alignment ring-shaped collimated light beam 2R, and then it follows the same light path as that of the alignment light beam and is directed to the focusing lens 5. The dichroic mirror 9D exhibits a maximum reflection factor and a minimum transmission to the wavelength of the photo-coagulation light 7, and exhibits a maximum transmission and a minimum reflection factor to the wavelength of the alignment light 2. A mirror 10 is obliquely arranged on the alignment optical axis between the second cone lens 4B and the dichroic mirror 9D inside of the alignment ring-shaped collimated light beam 2R. The reflected light of the alignment light which is reflected by the object plane of the eye and transmitted through the center portion of the dichroic mirror 9D is directed to an observation optical system 11 by the mirror 10.

In the embodiment of the present invention shown in FIG. 2, the reflected light of the photo-coagulation light which is reflected by the object plane of the eye and goes backward along the optical axis is prevented by the dichroic mirror 9D from being directed to the observation optical system 11. Accordingly, the eye of the observer is protected from the photo-coagulation light. On the other hand, the alignment light 2R which is formed into the ring-shaped collimated light beam by the second cone lens 4B passes through the periphery of the dichroic mirror 9D and then it is focused by the focusing lens 5 so that a light spot b or a ring-shaped light pattern c is formed on the object plane of the eye. The reflected light of the alignment light reflected by the object plane goes along the optical axis, passes through the focusing lens 5, passes through the center portion of the dichroic mirror 9D and is directed to the observation optical system 11 through the mirror 10. Thus, the light spot pattern b or the ring-shaped pattern a or b can be observed. If a portion of the light path of the photo-coagulation light is blocked by an iris of the eye to be treated, a portion of the ring-shaped pattern observed is dropped. Accordingly, the treatment area of the eye can be recognized by the drop of the pattern. Practically, the dichroic mirror 9D may be a half-mirror. In this case, however, a laser beam protection filter is needed for the observation system.

Like in the embodiment of FIG. 1, the alignment light and the photo-coagulation light may have the same numerical aperture so that the spot size by the alignment light in the in-focus state is equal to the spot size of the photo-coagulation. Accordingly, by observing the spot size through the observation optical system 11 at the time of alignment, the treatment portion on the object plane and the size thereof can be exactly estimated. The ring diameter of the ring-shaped collimated light beam may be increased by changing the distance between the cone lenses 4A and 4B so that the precision of the detection of the in-focus state is enhanced.

The alignment (focusing operation) along the optical axis may be automated by arranging a photo-sensing device such as a CCD in parallel to the observation optical system 11.

In the above embodiments, an optical system for rendering a refractive power of the eye to zero is additionally arranged on the light path between the eye to be treated and the focusing lens 5.

Figure 3A:
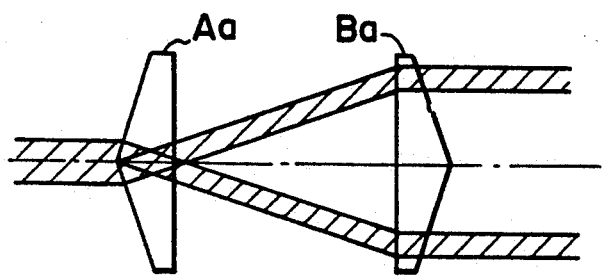
FIGS. 3A to 3E show various cone lens devices used in the ophthalmic optical apparatus of the present invention and light paths thereof.
Figure 3F:
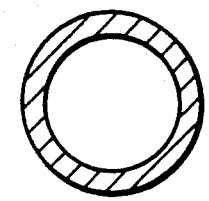
FIG. 3F shows a sectional view of a ring-shaped collimated light beam formed by the cone lens device of FIG. 2, FIGS. 4A and 4B show cone lenses each having two planes thereof formed conical and light paths thereof.
Figure 3B:
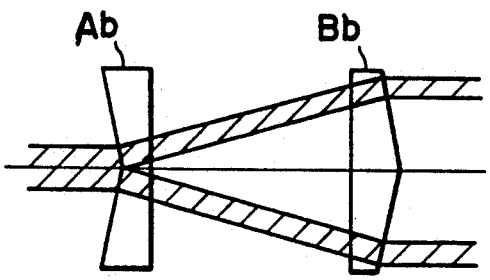
Figure 3C:
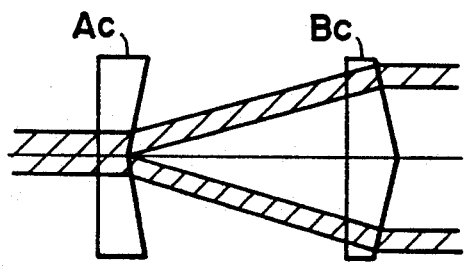
Figure 3D:
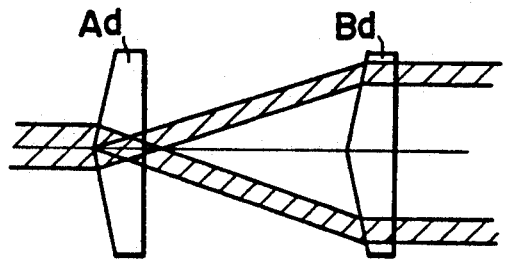
Figure 3E:
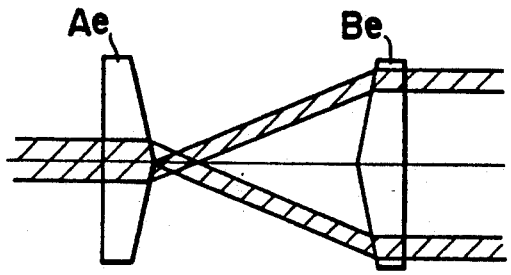
Figure 4A:
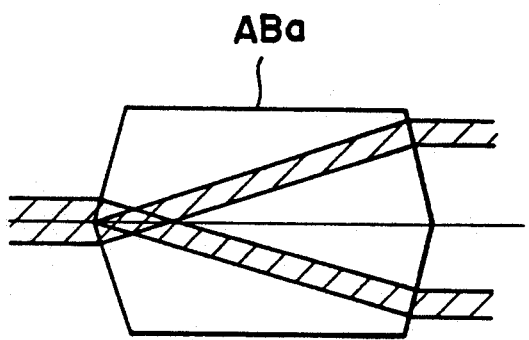
Figure 4B:
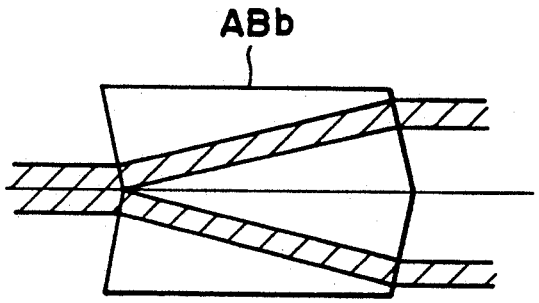
Figure 5:
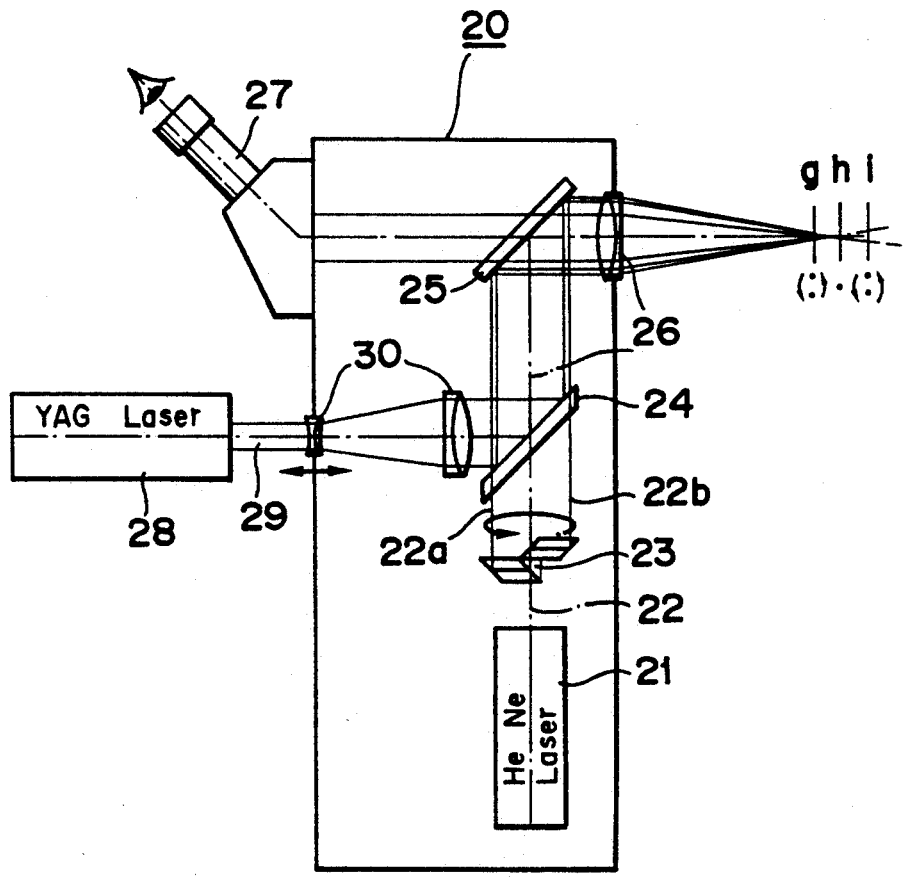
FIG. 5 shows a sectional view of a schematic construction of a prior art photo-coagulation apparatus.

In the above embodiments, the cone lens means comprising the two flat-convex cone lenses Aa and Ba as shown in FIG. 3A is used to form the ring-shaped collimated light beam as shown in FIG. 3F, although the cone lens means may be one of various combinations such as two flat-convex cone lens or a flat-concave cone lens and a flat convex cone lens as shown in FIGS. 3B and 3C. In FIGS. 3B and 3C, the first cone lens is a flat-concave cone lens Ab or Ac, and the second cone lens is a flat-convex cone lens Bb or Bc. In FIG. 3D, conical planes of two flat-convex cone lenses Ad and Bd are oriented in the same direction, and in FIG. 3E, conical planes of two flat-convex cone lenses Ae and Be face each other. As shown in FIGS. 4A and 4B, the cone lens means may be a bi-convex cone lens ABa having two conical planes or a meniscas cone lens ABb having a concave plane faced to a light source. When the bi-convex cone lens ABa or the meniscas cone lens ABb is used, it can be readily arranged on the alignment optical axis but the ring diameter of the ring-shaped collimated light beam is preset and not variable.

In accordance with the embodiment of the present invention, the exact focusing is attained with the simple alignment optical system having two conical planes and the light path of the treatment photo-coagulation light is secured. Further, since the distance between the two conical planes is variable, the precision of the detection of the in-focus state is enhanced.

When the present invention is applied to the photo-coagulation system as it is in the embodiment, the alignment light and the photo-coagulation light may have the same numerical aperture so that the size of the treatment point can be estimated from the spot size of the alignment light.

What is claimed is:

1. An ophthalmic optical apparatus having an alignment optical system, comprising:
   means for generating a treatment laser light beam;
   means for generating an alignment light beam having a different wavelength than that of the treatment light beam;
   a focusing optical system for focusing the treatment light beam and the alignment light beam onto an object plane of an eye to be treated; and
   cone lens means having two conical planes for expanding the alignment light beam to a collimated light beam having a ring-shaped cross section along a periphery of the treatment light beam;
   said cone lens means including a first conical plane arranged on the alignment optical axis for refracting the alignment light beam and expanding the same to a conical light beam centered on the optical axis, and a second conical plane for refracting the conical light beam, forming the same into a ring-shaped collimated light beam parallel to the optical axis and directly the same to said focusing optical system;
   whereby the alignment light beam is formed into a small light spot pattern in an in-focus state and into a ring-shaped light pattern centered on the optical axis in a defocus state.

2. An ophthalmic optical apparatus according to claim 1 wherein said cone lens means comprises two flat-convex cone lenses each having one plane thereof formed into a conical convex plane in said first conical plane and said second conical plane or a pair of cone lenses including a flat-concave cone lens having said first conical plane formed into a conical concave plane and a flat-convex cone lens having said second conical plane formed into a conical convex plane.

3. An ophthalmic optical apparatus according to claim 1 wherein said cone lens means comprises a biconvex cone lens having said first conical plane and said second conical plane formed into a conical convex plane, or a meniscas cone lens having a conical concave plane faced to a light source in said first conical plane and a conical convex plane faced to the focusing optical system in said second conical plane.

4. An ophthalmic optical apparatus according to claim 1 wherein said cone lens means comprises a first cone lens having said first conical plane and a second cone lens having said second conical plane, and at least one of said cone lenses is movable to permit the adjustment of a distance between said two conical planes in order to set a ring diameter of the ring-shaped collimated light beam.

5. An ophthalmic optical apparatus according to claim 1 further comprising a first mirror obliquely arranged on the optical axis inside of the ring-shaped collimated light beam for reflecting the treatment light beam toward said focusing optical system so that, in the in-focus state of the alignment light beam, the treatment light beam is focused to the same position as that of the light spot pattern of the alignment light beam.

6. An ophthalmic optical apparatus having an alignment optical system comprising:
 observation means for observing an object plane of an eye to be treated;
 means for generating a treatment laser light beam;
 means for generating an alignment laser light beam having a different wavelength than that of the treatment light beam;
 cone lens means including two conical planes arranged on the alignment optical axis for expanding the alignment light beam to a ring-shaped collimated light beam;
 a focusing optical system having an optical axis thereof coincide with the optical axis of said cone lens means for focusing the treatment light beam and the alignment light beam to an object plane of an eye to be treated;
 a first mirror arranged on the optical axis between said cone lens means and said focusing optical means to cross the ring-shaped collimated light beam for transmitting the alignment light beam therethrough and reflecting the treatment light beam toward said focusing optical system;
 said cone lens means including a first conical plane for refracting the alignment light beam and expanding the same to a conical light beam centered on the optical axis, and a second conical plane for refracting the conical light beam, forming the same into a ring-shaped collimated light beam parallel to the optical axis and directing the same to said focusing optical system, whereby the alignment light beam is formed into a small light spot pattern in an in-focus state and into a ring-shaped light pattern centered on the optical axis in a defocus state.

7. An ophthalmic optical apparatus according to claim 6 wherein said first mirror exhibits a maximum reflection factor to a wavelength of the treatment light beam and a minimum reflection factor to a wavelength of the alignment light beam, and exhibits a minimum transmission to the wavelength of the treatment light beam and a maximum transmission to the wavelength of the alignment light beam, whereby the treatment light beam reflected by the object plane of the eye to be treated is prevented from reaching said observation means and the alignment light beam reflected by the area of the eye to be treated is permitted to reach said observation means.

8. An ophthalmic optical apparatus according to claim 6 wherein said cone lens means comprises two flat-convex cone lenses each having one plane thereof formed into a conical convex plane in said first conical plane and said second conical plane or a pair of cone lenses including a flat-concave cone lens having said first conical plane formed into a conical concave plane and a flat-convex cone lens having said second conical plane formed into a conical convex plane.

9. An ophthalmic optical apparatus according to claim 6 wherein said cone lens means comprises a biconvex cone lens having said first conical plane and said second conical plane formed into a conical convex plane, or a meniscas cone lens having a conical concave plane faced to a light source in said first conical plane and a conical convex plane faced to the focusing optical system in said second conical plane.

10. An ophthalmic optical apparatus according to claim 6 wherein said cone lens means comprises a first cone lens having said first conical plane and a second cone lens having said second conical plane, and at least one of said cone lenses is movable to permit the adjustment of a distance between said two conical planes in order to set a ring diameter of the ring-shaped collimated light beam.

11. An ophthalmic optical apparatus according to claim 6 further comprising a second mirror obliquely arranged on the alignment optical axis between said cone lens means and said first mirror so that the reflected light of the alignment light beam reflected by the object plane of the eye to be treated and transmitted through the first mirror is directed to said observation means.

* * * * *